United States Patent [19]

Kidman et al.

[11] Patent Number: 4,847,409

[45] Date of Patent: Jul. 11, 1989

[54] RECOVERY OF L-AMINO ACID ISOMERS FROM THEIR RACEMIC MIXTURES

[75] Inventors: Gene E. Kidman, Ubly; William E. Gardner, Bad Axe, both of Mich.

[73] Assignee: The NutraSweet Company, Deerfield, Ill.

[21] Appl. No.: 284,042

[22] Filed: Dec. 14, 1988

[51] Int. Cl.$^4$ .............................................. C07B 57/00
[52] U.S. Cl. ..................................... 562/401; 562/402
[58] Field of Search ................................ 562/401, 402

[56] References Cited

U.S. PATENT DOCUMENTS

| | | | |
|---|---|---|---|
| 2,556,917 | 6/1951 | Hambrock | 562/402 |
| 2,657,230 | 10/1953 | Rogers | 562/401 |
| 4,613,688 | 9/1986 | Inone et al. | 562/401 |

Primary Examiner—Paul J. Killos
Assistant Examiner—Vera C. Clarke
Attorney, Agent, or Firm—Craig M. Bell

[57] ABSTRACT

A method for the isolation of a substantially pure L-isomer of an amino acid from its D,L racemic mixture does not require the use of a resolving agent, the formation of a derivative of the amino acid or additional enzymic reactions. The method is based upon the concept of the equal saturation point wherein the L-isomer can be separated from the D-isomer by precipitation of the L-isomer when the relative concentration of the D-isomer is less than 7.0% or by precipitation of the D,L racemate when the relative concentration is greater than 7.0%. Selective crystallization through seeding allows for further isolation of pure L-isomer when its relative concentration in solution is very low.

40 Claims, 3 Drawing Sheets

RECOVERY OF L-PHENYLALANINE FROM RACEMATE

RECOVERY OF L-AMINO ACID ISOMERS FROM THEIR RACEMIC MIXTURES

BACKGROUND OF THE INVENTION

Amino acids are important food additives in both human and animal diets and their production and purification have become vital to numerous food industries. Many amino acids are made either chemically or through fermentation processes which require the separation and isolation of the desired amino acids from the broth.

Many amino acids exist as two optically active enantiomers, the L and D-isomers. It is often preferred in many applications to separate the two from their racemic mixture that is produced during chemical processing. L-phenylalanine for example, is a component of the popular dipeptide sweetener aspartame, technically known a alpha-L-aspartyl-L-phenylalanine methyl ester (APM). It is also known that when the dipeptide is comprised of the two L-isomers of aspartic acid and phenylalanine, it is sweet, whereas their D-L, L-D, D-D etc. enantiomers are not. Moreover, any of the enantiomers which contain D-phenylalanine are worthless as sweeteners.

Aspartame can by synthesized by any one of several biochemical processes but these generally involve a coupling reaction whereby aspartic acid is joined with either phenylalanine or its methyl ester. Hence, the finished product must be separated from its enantiomers and any unreacted phenylalanine and aspartic acid. It is economically advantageous to conserve L-phenylalanine by hydrolysing the non-sweet esters and recovering the phenylalanine. However, during the various chemical process steps used to make APM and recover the leftover phenylalanine, some of the L-phenylalanine is racemized. Therefore, when this phenylalanine is recovered, it contains some of the D-isomer. Since the D-isomer cannot be utilized in the manufacture of the dipeptide sweetener, it would be useful to be able to separate the L-phenylalanine isomer as economically as possible from the racemic mixture.

It is an object of the present invention to crystallize and isolate pure L-isomers of an amino acid from a racemic mixture when the racemate has more of the L-isomer than the D-form. More specifically, it is an object of the present invention to obtain pure L-phenylalanine from a racemic mixture comprised of both the L- and D-forms.

Various methods for separating the L and D isomers, are known and generically are referred to as resolution. The most common method of resolving D,L-mixtures involves combining them with an optically active compound known as a resolving agent, followed by fractional crystallization of the resulting mixture of compounds (diastereroisomers) in solution. For practical resolution, it is necessary to find a combination of resolving agent and solvent which will give good crystallization behavior together with a pronounced difference in solubility between the diastereoismers. Examples of this technique as applied to the resolution of an amino acid are in U.S. Pat. Nos. 2,556,907, Emmick, R., and 2,657,230, Rogers, A. These patents discuss methods to resolve D, L-lysine in which optically active glutamic acid is employed as the resolving agent.

More recently, phenylalanine has been resolved by enzymatic hydrolysis of its diastereroisomers. The enzyme, chymotrypsin, selectively hydrolyzes L-phenylalanine esters. Hence L-phenylalanine is recovered from a mixture of the D,L-phenylalanine ester. An example of this process is Eur. Pat. Appl. No. EP 174,862, Empie, M., (8/17/84).

However, the aforementioned methods of the prior art require an additional step beyond that of the fermentation involving the use of a resolving agent in a chemical or enzymatic reaction or some combination of these to form a derivative of phenylalanine in order to isolate the desired isomer. The present invention permits the separation of the L-isomer from the racemic mixture and in the same step, its purification from other amino acids, salts, etc., without the requirement of a resolving agent, the subsequent formation of a derivative of the amino acid in question and without enzymatic reaction.

SUMMARY OF THE INVENTION

A method for the selective crystallization of the L-isomer from a D, L mixture of amino acid isomers is described. More specifically, a method is set forth for the selective crystallization of L-phenylalanine. Further, a method is described to prepare a mother liquor rich in L-phenylalanine by crystallizing and separating the isomers of the racemate, then selectively crystallizing L-phenylalanine from this liquor. Pure L-phenylalanine cay be crystallized from racemate under a vacuum at temperatures between approximately 5.0° C. and 65.0° C. if after crystallization the D-phenylalanine is about 7.0% or less of the total phenylalanine left in solution. A racemate crystal comprised of approximately 50% D- and 50% L-phenylalanine can be crystallized from racemate at the above temperatures if after crystallization the D-phenylalanine is about 7.0% or more of the total phenylalanine left in solution. Crystallization conditions must include slow crystal growth and crystal digestion to assure the desired composition of crystals of pure L-phenylalanine or of 50% racemate. When the ratio of the D-isomer to total phenylalanine is about 7.0% or greater, further precipitation of L-phenylalanine which is contaminated with less than 7.0% D-phenylalanine is possible between approximately 5.0° C. and 55.0° C., if the solution is seeded with pure L-phenylalanine, followed by a digestion time, and then slow crystallization.

DETAILED DESCRIPTION OF THE INVENTION

The present invention is based on the fact that the D- and L-isomers of phenylalanine combine to form racemic crystals of phenylalanine that are only half as soluble as either of the two isomers alone. The presence of excess L-phenylalanine reduces the solubility of the D,L phenylalanine complex. Surprisingly, there is a limit to this effect and the limit occurs at approximately the same relative ratio of D-phenylalanine to total phenylalanine (D/T) under a range of temperature of solution or solution concentrations of total phenylalanine. This phenomena will be referred to as "the limit ratio" or the "equal saturation point." At this limit, the physical state of the solution may be described as being saturated with L-phenylalanine and the D,L-phenylalanine complex.

Surprisingly, at relatively low levels of D-phenylalanine, below the limit ratio, pure L-phenylalanine crystals will precipitate upon evaporative crystallization. This will continue until the relative solution concentration of D-phenylalanine rises to become approximately 7.0% of the total phenylalanine in solution (D/T≅7.0%). Pure L-phenylalanine can be crystallized from racemate under a vacuum at temperatures between approximately 5.0° C. and 65.0° C. if before crystallization the D/T is less than 7.0% and after crystallization the D/T is about 7.0% in solution.

At higher relative concentrations of D-phenylalanine in the racemic mixture, i. e. where the D/T >7.0%, a racemic D,L crystal precipitates upon evaporative crystallization until the relative concentration of D-phenylalanine is reduced to about 7.0% A racemate crystal comprised of approximately 50% D- and 50% L-phenylalanine can be crystallized from the racemate mixture between approximately 5.0° C. and 100° C. if, before crystallization, the D/T is above 7.0% and after crystallization the D/T is greater than or equal to about 7.0% in solution. To assure the desired composition of crystals of pure L-phenylalanine or of the 50% racemate, crystallization and crystal digestion should be conducted at a slow rate.

Figure 1:
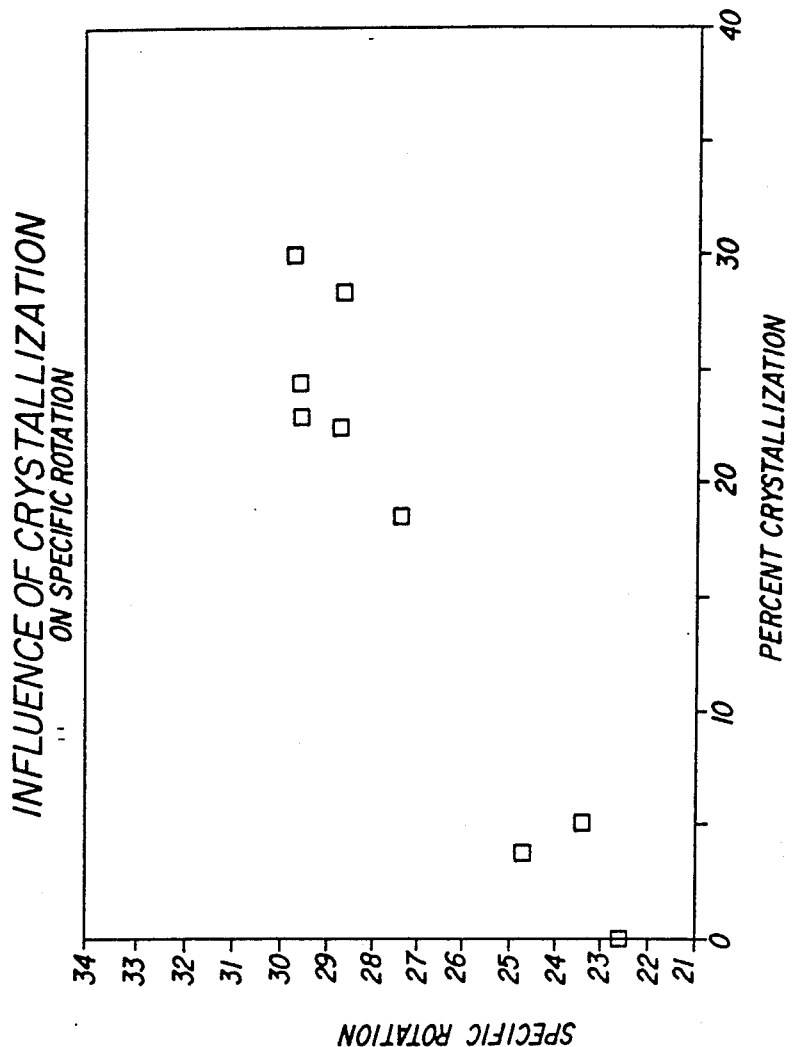
FIG. 1 relates to the enrichment of L-phenylalanine in solution phase.

FIG. 1 illustrates the enrichment of L-phenylalanine in the solution phase by precipitation of the racemate. Various weights of phenylalanine were added to water and the volume of water was brought to 1 liter after dissolution of the sample. The solutions were cooled to approximately 50° C. and then filtered. The phenylalanine batched into the experiment was 17.35% D-phenylalanine (i.e., high D-isomer concentration). The x-axis is the percent of the phenylalanine which was precipitated out of solution. The y-axis is the specific rotation of the phenylalanine in the resultant solution phase. The resultant solution concentration of phenylalanine was approximately equal in all cases and was approximately 45 gm/l. This supports the existence of the equal saturation point or limit ratio of D/T in solution, since the specific rotation of the phenylalanine in solution rises as more phenylalanine precipitates, but only to a certain point.

Figure 2:
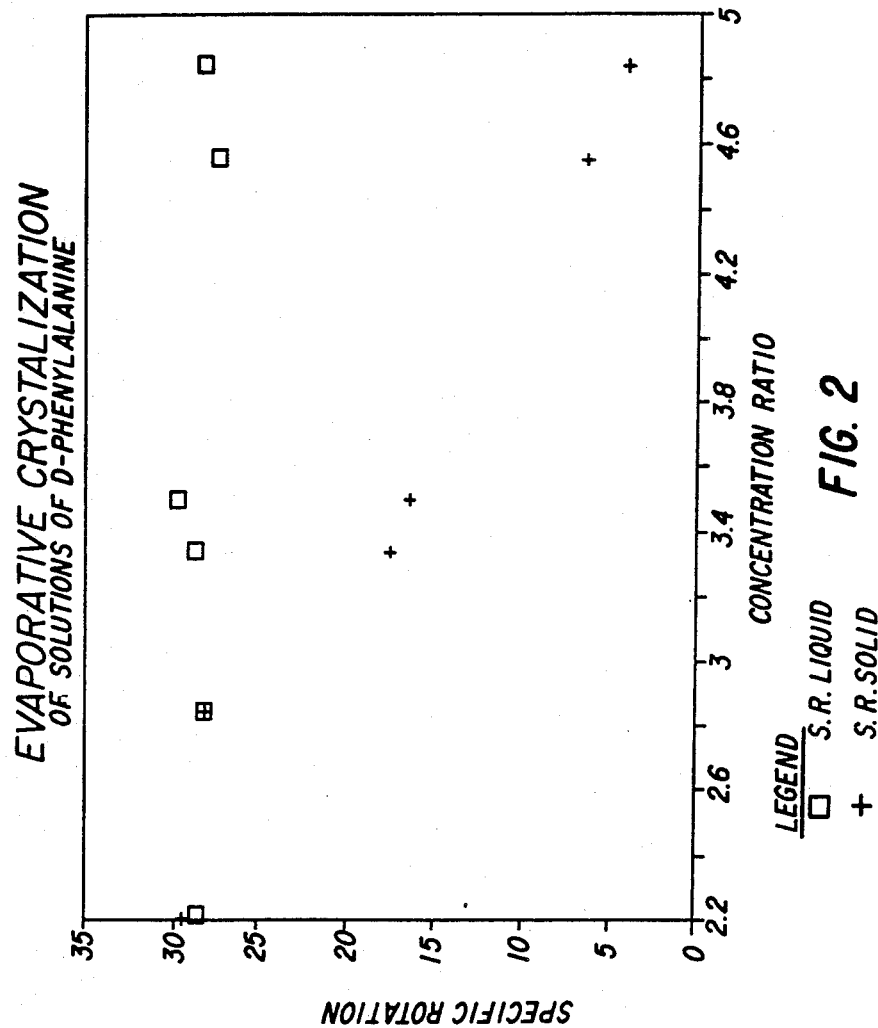
FIG. 2 relates to evaporative crystallization of solutions of D-phenylalanine.

In FIG. 2, the starting solution was at the equal saturation point. The specific rotation (S.R.) of the phenylalanine in the solid phase can be compared to that in the solution phase. At low evaporation ratios, the specific rotation of phenylalanine in either phase is the same. The composition of the liquid and solid phases should therefore remain equal as a solution at the equal saturation point is concentrated. An unexpected observation is that racemization occurs with further concentration. Moreover, the extent of racemization is proportional to the extent of evaporation. The S.R. of the solution phase doesn't change with the extent of evaporation which facts supports the existence of an equal saturation point or limit ratio of D/T.

When the D/T is about 7.0%, further precipitation of phenylalanine from solution maintains the relative solution concentration of the isomers. Hence, a racemic solution with an enantiomeric excess of L-phenylalanine will produce either pure L-phenylalanine, a racemate composed of 50% D- and 50% L-phenylalanine or a mixture of the two crystal compositions.

However, the composition of the crystal phase might be effected by kinetic factors. If there are little or no racemate crystals upon which the crystallization process can build, but there is an excess of L-phenylalanine crystals, then L-phenylalanine crystallization is carried out and the relative concentration of D-phenylalanine in solution would increase. Digestion in the presence of pure L-phenylalanine seed favors crystallization of L-phenylalanine and a rise in the relative concentration of D-phenylalanine in solution. When the ratio of D- to total phenylalanine is about 7.0%, further precipitation of L-phenylalanine with less than 7.0% D-phenylalanine is possible between approximately 5.0° C. and 55.0° C. if the solution is seeded with pure L-phenylalanine, followed by digestion and then slow crystallization.

By combining processes of (1) precipitation of pure L-phenylalanine, (2) precipitation of a racemate composed of 50% D- and 50% L-phenylalanine and (3) selective crystallization, it is possible to separate excess L-phenylalanine from a less than 50% racemate, so that the result of the separation is a nearly 50% racemate on the one hand and nearly pure L-phenylalanine on the other. It is therefore possible to make racemate at any lesser level of D-phenylalanine.

A model of the relationship of the D-phenylalanine in starting material to D-phenylalanine in the crystal product, and to D-phenylalanine in the mother liquor exists in the following equation. If the starting material has a very low D/T, this equation can be used to predict how much L-phenylalanine can be precipitated before it would likely become unacceptably contaminated by D-phenylalanine due to further precipitation. At very high D/T, it can predict how much racemate can be precipitated to maximize the L-phenylalanine enrichment of the mother liquor.

$$\%Dt = \% Dp(\%P) + 0.07(\% S)$$

Where:
%Dt = relative percent D-phenylalanine in starting material,
%Dp = relative percent D-phenylalanine in product,
%P = percent of starting material in product,
%S = percent of starting material left in solution, and
0.07 = the estimate of the relative percent D-phenylalanine at the equal saturation point.

For example, if the starting material contains 3.0% D-phenylalanine and as much as 1.5% D-phenylalanine would be acceptable in the product, it would be possible to dissolve and reprecipitate approximately 73% of the starting material as product. In another embodiment, if the starting material had 30% D-phenylalanine and the racemate would be expected to contain 47% D-phenylalanine, then the recovery of L-phenylalanine enriched solution can be maximized at 7.0% by dissolving and precipitating approximately 57.5% of the starting material as racemate product.

Another embodiment of the invention is the recovery of an L-phenylalanine enriched fraction from a racemic mixture by selective crystallization. The racemic mixture could be an L-phenylalanine enriched mother liquor which could be created as in the second example in the previous paragraph. This method involves the addition of an L-phenylalanine seed and a period of time for digestion of the seed crystals. This method favors enrichment of L-phenylalanine in the precipitate and affects the relative rate of growth of the two crystals.

Figure 3:
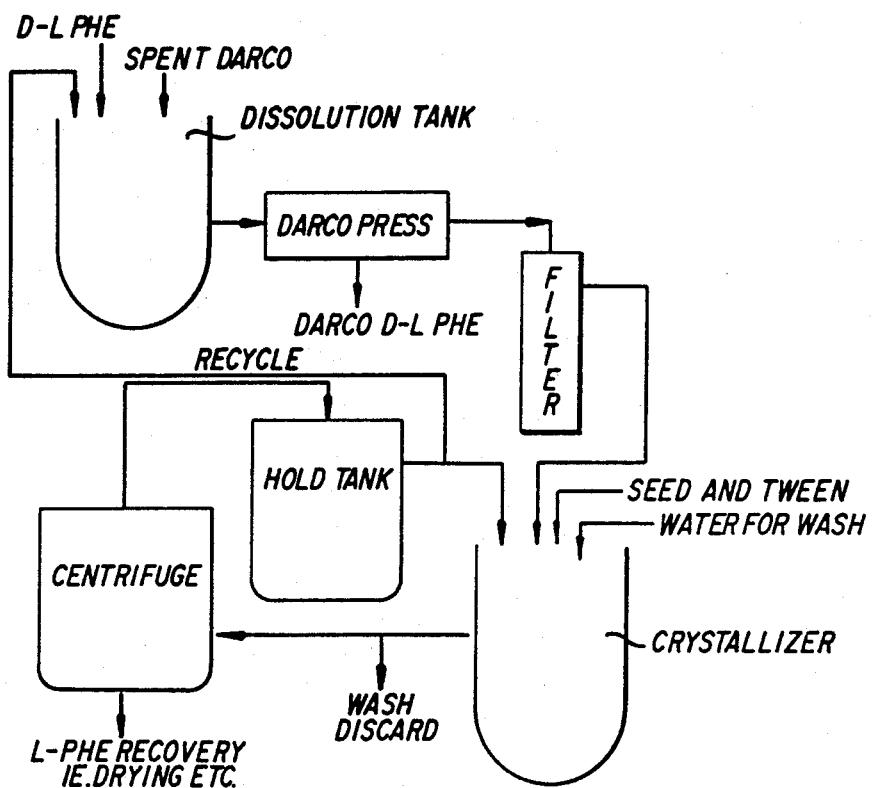
FIG. 3 relates to a schematic representation of the recovery of L-phenylalanine from the racemate.

FIG. 3 represents a general schematic representation of how the above methodologies may be combined in a commercial process. The starting material is D,L-phenylalanine recovered from an aspartame (APM) mother liquor. The D,L-phenylalanine is batched into the dissolution tank and combined with any recycled mother liquor. The solution is heated to a temperature range of approximately 60°–100° C., preferably the upper limit of 95°–100° C. in order to insure that most of the L-phenylalanine is dissolved into solution. It is then possible to dissolve L-phenylalanine out of an otherwise approximately 50% D-phenylalanine racemate without totally dissolving the racemate. When the solution is cooled, the racemate is removed, leaving an L-phenylalanine enriched mother liquor. The temperature at which the racemate is removed should be approximately the same as that of the crystallizer during the digestion period. Darco carbon may optionally be added and mixed with the solution in the dissolution tank. The carbon can be removed with the racemate and the two may be removed by any standard filtration device such as the darco press known in the art. Carbon treatment of the mother liquor removes impurities which may interfere with crystallization or diminish the quality of the L-phenylalanine product.

The amount of phenylalanine to be batched into the dissolution tank must be calculated by taking into account the D-phenylalanine concentration of both the starting material and of the recycled mother liquor. The D/T of these combined sources is %D in the following equation. The racemate which is removed to produce the L-phenylalanine enriched mother liquor is the DL-loss in the equation. This percentage is also the amount of phenylalanine above that required to obtain the solution concentration desired in the crystallizer which must be batched into the dissolution tank. This equation is derived from the previous equation where the mother liquor is estimated to contain 7.0% D-phenylalanine and the racemate is estimated to contain 47% D-phenylalanine.

$$\text{DL-loss } \% = ((\%D \times 100) - 700)/40$$

For example, if the starting material had 30% D-phenylalanine and racemate, 57.5% of the material is precipitated as racemate. This is as in the previous example. If the digestion temperature is 50.0° C., then the solution concentration desired is about 45 gm/l. Therefore, the concentration to be batched in the dissolution tank is 106 gm/l.

Before transferring the L-phenylalanine enriched mother liquor to the crystallizer, the crystallizer and transfer lines should be heated slightly above the digestion temperature, since any sudden cooling of any part or portion of the racemate solution may result in the formation of the wrong crystal type.

The mother liquor, once transferred to the crystallizer is then seeded with a generous dose of pure L-phenylalanine crystals in order to initiate precipitation of pure L-phenylalanine from solution. This is followed by the addition of a Tween surfactant and a digestion period. The digestion temperature is preferably approximately 45.0° to 65.0° C. but may range from approximately 20.0° C. to 65.0° C. Digestion improves the purity of L-phenylalanine which is subsequently crystallized out of solution. The Tween removes some of the interstitial water. The crystals are formed by slowly cooling the solution.

The L-phenylalanine crystals thus formed are centrifuged and removed from the mother liquor as it is cooled to approximately 15.0°–25.0° C., preferably 20.0° C., and the crystals are removed as they precipitate. Failure to remove the crystals in this manner may result in an unmanageably thick slurry. During crystallization, the mother liquor is recycled back into the crystallizer from the centrifuge to maximize crystal recovery. When crystallization is complete, and no more crystals can be recovered, the mother liquor is recycled to the dissolution tank for the next batch. Before repeating the process, it is important to wash the crystallizer, centrifuge and process lines to remove any remaining crystal. The wash may be discarded. The presence of any remaining crystal may subsequently interfere with selective crystallization.

Other embodiments of the present invention is a process for the co-recovery of L-phenylalanine from racemate and of L-phenylalanine from fermentation broth. The L-phenylalanine is recovered by evaporative crystallization, followed by re-dissolution, treatment of the dissolved phenylalanine with carbon to remove any impurities and recrystallization. Each crystallization leaves a mother liquor, all or part of which is discarded. The discarded liquor can be used as a bleed stream for D-phenylalanine. The maximum bleed required is such that all of the D-phenylalanine which is produced during the recovery and added to the recovery stream leaves with the discarded liquor. This can be accomplished if the D-phenylalanine in the discarded liquor is no more than 7.0% of the total phenylalanine in this stream (i.e. D/T≦7.0%). Under some conditions, the D/T of the mother liquor can be higher.

Pure L-phenylalanine can also be recovered from the mother liquor by converting the phenylalanine present as a racemate to its salt. By doing this, the solubility of the 50% D-phenylalanine racemate will increase. For example, the solubility of the racemate increases under each of the following conditions:

(1) when NaOH is used to give a solution of 50% racemate a high pH,
(2) $NaHCO_2$ is added and heated to produce a sodium salt of the 50% racemate, or
(3) acetic acid is used to give a solution of 50% racemate a low pH.

As a sodium salt, the racemate is twice as soluble as pure L-phenylalanine under the same conditions. A high concentration of salt may also cause this apparent increase in racemate solubility.

However, without selective crystallization, excess L-phenylalanine, precipitated under conditions described in the above paragraph, is not pure and usually has only a slightly reduced D/T as compared to the solution's D/T before crystallization.

By using the principles of selective crystallization, excess L-phenylalanine can be precipitated as pure L-phenylalanine and the D/T of the waste stream can exceed 7.0%. Hence, during evaporative crystallization of a low D/T racemate, in the presence of a high concentration of ammonium sulfate, the average D/T of the mother liquor may increase as the salt concentration increases and a pure L-phenylalanine can be recovered. However, the total solubility of phenylalanine in the mother liquor will also decrease. The disadvantage of this higher D/T in the mother liquor is that these solutions become less stable as the D/T increases, and therefore can suddenly precipitate out 50% racemate to contaminate otherwise pure L-phenylalanine. Therefore, even with selective crystallization it is best if the mother liquor D/T is not in excess of much more than 7.0% (i.e. D/T≦15.0%)

The following examples are set forth in order to better demonstrate the preferred embodiments of the present invention. They are for illustrative purposes only and are not intended to limit the spirit and scope of the invention as recited in the claims that follow.

EXAMPLE 1

A racemic mixture containing 30% of the D-isomer was dissolved in fifteen (15) liters of water to a concentration of 30 gm/l at a temperature of 80° C. and a pH of approximately 4.5. At this pH, the non-hydrated form of the L-phenylalanine isomer dominates. The solution was fed into the crystallizer and for every five liters of solution, 3.750 liters of water was removed by evaporation at 55° C. under vacuum. The concentrate was then cooled to 50° C. and filtered producing an L-phenylalanine rich mother liquor. The mother liquor from three batches prepared in this manner were combined and one liter of water was added to this. A second evaporative crystallization was then carried out at 80° C. under vacuum until 2.75 liters of water were removed. One gram of L-phenylalanine was added as a seed for crystallization when an additional 2.4 liters of water had been removed by evaporation. This final concentrate was filtered and the crystals that had precipitated out of solution were removed.

The first batch of crystals filtered out of solution weighed 273.85 gm and had a specific rotation of −13.5. These were found to be comprised of the D,L isomer as expected. The second batch of crystals precipitated out of solution weighed 46.17 gm and was found to have a specific rotation of −32.3. This was found to be comprised 99.7% pure L-phenylalanine.

EXAMPLE 2

Several L-phenylalanine purification runs were conducted according to the recovery procedure outlined as FIG. 3. The D,L racemate was batched into the dissolution tank at the relative concentrations of D-phenylalanine as set forth below for three separate lot runs. Each lot was then processed according to the present invention through four cycles. The numbers listed are in grams. The relative concentration of D-phenylalanine in the starting material is shown in parenthesis.

|  | CYCLE I | CYCLE II | CYCLE III | CYCLE IV |
|---|---|---|---|---|
| INPUT |  |  |  |  |
| Lot A | 8871.01 (16.8%) | 3617.22 (20.1%) | 3617.22 (20.1%) | 3617.22 (20.1%) |
| Lot B | 2565.90 | 3614.91 | 3614.91 | 3614.91 |
| Lot C | 4489.74 | 3614.80 | 3614.80 | 3614.80 |
| Recycle | — | 6540.88(a) | 6645.45(b) | 6297.45(c) |
| Darco Press Blow Out | — | 1169.66 | 944.17 | 1552.32 |
| Seed (L-phe) | 23.00 | 23.00 | 23.00 | 23.00 |
| Total | 15949.65 | 18580.47 | 18459.55 | 18719.70 |
| Output | 105 |  |  |  |
| DL-Phe | 3245.20 | 7586.44 | 6717.85 | 7986.72 |
| Darco Press Blow Out | 1169.66 | 944.17 | 1552.32 | 1547.26 |
| Recycle | 6540.88 (a) | 6645.45 (b) | 6297.45 (c) | 6592.49 |
| L-Phe Pure | 419.62 | 3692.65 | 3409.08 | 2940.99 |
| Total | 15146.36 | 18868.71 | 17976.70 | 19067.46 |
| % D-Phe in Pure L-Phe Recovery Fraction | 1.08 | 1.21 | 1.10 | 1.91* | a, b, and c represents grams of phenylalanine that was recycled.
Cycle I had no recycled phenylalanine in the initial batch.

It is clear from the above data that a recovery of substantially pure L-phenylalanine can be expected by the methods of the present invention. With starting material containing an extreme excess of enantiomeric L-phenylalanine it is possible to apply the principle of equal saturation point that leaves the D-phenylalanine in solution while precipitating substantially pure L-phenylalanine. When the starting material contains lesser relative concentrations of L-phenylalanine it is possible to use the equal saturation point to precipitate the D,L racemic crystal from solution leaving the motor liquor enriched with L-phenylalanine. The desired L-isomer can then be purified and isolated from the mother liquor by selective crystallization. The method may also be practiced in the crystallization and purification of other amino acids with slight variations in the procedure.

What I claim is:

1. A method for the isolation of a substantially pure L-isomer of an amino acid from its D,L racemic mixture comprising the steps of:
    (a) dissolving said racemate into solution;
    (b) evaporating said solution for a time sufficient to slowly precipitate a crystal until the relative concentration of the D-isomer in solution is approximately 7.0%;
    (c) selectively crystalling the L-isomer of said amino acid by slowly seeding the solution with a sufficient amount of L-isomer crystal so as to instigate further precipitation of crystal;
    (d) heating the mixture at a sufficient temperature to digest said L-isomer crystals;
    (e) cooling said mixture to re-precipitate said L-isomer crystals; and
    (f) removing said L-isomer crystals from solution.

2. The method of claim 1 wherein said D,L racemic mixture is dissolved at a temperature in the range of approximately 60°-100° C.

3. The method of claim 2 wherein said solution is slowly evaporated under a vacuum at a temperature of approximately 40°-80° C.

4. The method of claim 3 wherein said temperature is approximately 45°–55° C.

5. The method of claim 4 wherein the L-isomer crystal is digested by slowly heating at a temperature of approximately 20° C. to 65° C.

6. The method of claim 5 wherein said temperature is approximately 45° C. to 65° C.

7. A method for the isolation of a substantially pure L-phenylalanine fraction from a racemic mixture of phenylalanine with a high L/D isomeric ratio comprising the steps of:
(a) dissolving said racemate into solution;
(b) evaporating said solution for a time sufficient to slowly precipitate substantially pure L-phenylalanine until the relative concentration of D-phenylalanine in solution reaches 7.0%;
(c) selectively crystallizing L-phenylalanine by slowly seeding the solution with a sufficient amount of L-phenylalanine crystal so as to instigate further precipitation of L-isomer crystal;
(d) heating the mixture at a sufficient temperature to slowly digest said L-isomer crystals;
(e) cooling said mixture to re-precipitate substantially pure L-phenylalanine crystals; and
(f) removing said crystals from solution.

8. The method of claim 7 wherein said L/D isomer ratio is at least 93:7.

9. The method of claim 8 wherein said D,L racemic mixture is dissolved at a temperature in the range of approximately 60° C. to 100° C.

10. The method of claim 9 wherein said solution is recycled mother liquor.

11. The method of claim 10 wherein said solution is slowly evaporated under a vacuum at a temperature of approximately 40° C. to 80° C.

12. The method of claim 11 wherein said temperature is approximately 45° C. to 55° C.

13. The method of claim 12 wherein the L-phenylalanine crystal is slowly digested by heating said mixture to a temperature of approximately 20° C. to 65° C.

14. The method of claim 13 wherein said temperature is approximately 45° C. to 65° C.

15. The method of claim 13 further comprising the addition of a surfactant prior to said re-precipitation of the substantially pure L-phenylalanine crystals.

16. A method for the isolation of a substantially pure L-phenylalanine fraction from a racemic mixture of phenylalanine with a low L/D isomer ratio comprising the steps of:
(a) dissolving said racemate into solution;
(b) evaporating said solution for a time sufficient to precipitate a D,L-phenylalanine racemic crystal until the relative concentration of D-phenylalanine in solution reaches approximately 7.0%;
(c) removing said precipitate from solution;
(d) selectively crystallizing the remaining L-phenylalanine in solution by slowly seeding the solution with a sufficient amount of L-phenylalanine crystal so as to instigate precipitation;
(e) heating the solution at a sufficient temperature to slowly digest the L-phenylalanine crystals;
(f) cooling said solution to reprecipitate substantially pure L-phenylalanine crystals; and
(e) removing said crystals from solution.

17. The method of claim 16 wherein the relative concentration of D-phenalanine in said D,L racemic mixture is approximately 8.0–50.0%.

18. The method of claim 17 wherein said D,L racemic mixture is dissolved in solution at a temperature in the range of approximately 60° C. to 100° C.

19. The method of claim 18 wherein said solution is evaporated under a vacuum at a temperature of approximately 40° C. to 60° C.

20. The method of claim 19 wherein said temperature is approximately 45° C. to 55° C.

21. The method of claim 20 wherein said L-phenylalanine crystals are slowly digested by heating the mixture to a temperature of approximately 20° C. to 65° C.

22. The method of claim 21 wherein said temperature is approximately 45° C. to 65° C.

23. The method of claim 17 wherein said solution is recycled mother liquor.

24. The method of claim 23 wherein said recycled mother liquor is recovered from a previous selective L-phenylalanine crystallization.

25. The method of claim 23 wherein said recycled mother liquor is recovered from an aspartame synthesis reaction.

26. The method of claim 17 further comprising the addition of a metal salt to said racemic mixture.

27. The method of claim 26 wherein said metal salt is sodium hydroxide.

28. The method of claim 26 wherein said metal salt is sodium carbonate.

29. The method of claim 17 further comprising the addition of acetic acid to said D,L racemic mixture.

30. A method for the isolation of a substantially pure L-phenylalanine fraction from a racemic mixture of phenylalanine comprising the steps of:
(a) dissolving said racemate into solution;
(b) precipitating a first crystal type until the relative concentration of D-phenylalanine in solution reaches approximately 7.0%;
(c) selectively crystallizing L-phenylalanine by slowly seeding the solution with a sufficient amount of L-phenylalanine crystal so as to instigate further precipitation of L-isomer crystal;
(d) heating the mixture at a sufficient temperature to slowly digest said L-isomer crystals;
(e) cooling said mixture to re-precipitate substantially pure L-phenylalanine crystals; and
(f) removing said crystals from solution.

31. The method of claim 30 wherein said racemate is dissolved in solution at a temperature in a range of approximately 60° C.–100° C.

32. The method of claim 31 wherein said first crystal type is precipitated by cooling said solution to a temperature in a range of approximately 40° C.–60° C.

33. The method of claim 31 wherein said racemic mixture is comprised of a high L/D isomer ratio.

34. The method of claim 33 wherein said first crsytal type is comprised of substantially pure L-phenylalanine.

35. The method of claim 31 wherein said racemic mixture is comprised of a low L/D isomer ratio.

36. The method of claim 35 wherein said first crystal type is comprised of D,L phenylalanine racemate.

37. The method of claims 34 or 36 wherein the L-phenylalanine crystal is slowly digested by heating said mixture to a temperature of approximately 20° C. to 65° C.

38. The method of claim 37 wherein said temperature is approximately 45° C. to 65° C.

39. The method of claim 38 wherein said pure L-phenylalanine is re-precipitated by cooling said solution to a temperature range of approximately 40° C. to 60° C.

40. The method of claim 39 further comprising the addition of a surfactant prior to said re-precipitation of the substantially pure L-phenylalanine crystals.

* * * * *